(12) United States Patent
Wu et al.

(10) Patent No.: US 12,005,177 B2
(45) Date of Patent: *Jun. 11, 2024

(54) SELF-SEALING CANNULA

(71) Applicant: University of Maryland, Baltimore, Baltimore, MD (US)

(72) Inventors: Zhongjun Wu, Marriottsville, MD (US); Bartley P. Griffith, Gibson Island, MD (US); Keshava Rajagopal, Sugar Land, TX (US)

(73) Assignee: University of Maryland, Baltimore, Baltimore, MD (US)

( * ) Notice: Subject to any disclaimer, the term of this patent is extended or adjusted under 35 U.S.C. 154(b) by 952 days.

This patent is subject to a terminal disclaimer.

(21) Appl. No.: 16/891,655

(22) Filed: Jun. 3, 2020

(65) Prior Publication Data
US 2020/0405944 A1  Dec. 31, 2020

Related U.S. Application Data

(63) Continuation of application No. 15/526,107, filed as application No. PCT/US2015/060127 on Nov. 11, 2015, now Pat. No. 10,695,483.
(Continued)

(51) Int. Cl.
*A61M 1/36* (2006.01)
*A61B 17/00* (2006.01)
*A61B 17/34* (2006.01)
*A61M 60/178* (2021.01)
*A61M 60/38* (2021.01)
(Continued)

(52) U.S. Cl.
CPC ....... *A61M 1/3659* (2014.02); *A61B 17/3417* (2013.01); *A61B 17/3421* (2013.01); *A61B 17/3439* (2013.01); *A61M 60/178* (2021.01); *A61M 60/38* (2021.01); *A61M 60/857* (2021.01); *A61M 60/861* (2021.01); *A61B 2017/00247* (2013.01);
(Continued)

(58) Field of Classification Search
CPC ........ A61B 17/3421; A61B 2017/3419; A61B 17/3417; A61B 17/3439; A61B 2017/00247; A61M 1/1008; A61M 1/3659; A61M 60/857; A61M 60/148
See application file for complete search history.

*Primary Examiner* — Leslie R Deak
(74) *Attorney, Agent, or Firm* — Whiteford, Taylor & Preston, LLP; Gregory M. Stone

(57) ABSTRACT

The present invention discloses a self-sealing cannula and methods of its use. The self-sealing cannula can be minimally invasively placed into the heart for drawing and/or returning blood with a self-sealing function at the interface of the blood access site. The disclosed cannula can be implemented as a single lumen cannula or a double lumen cannula, which can be used with ventricular assist devices for heart support or pump-oxygenators for ECMO and respiratory support. Through a self-sealing mechanism fixed on the ventricular wall or atrial wall, a cannula body is attached to the self-sealing fixture and blood is drawn into the lumen via an external pump and returned to the circulation system through a separate cannula. In the case of the double lumen cannula embodiment, the blood will be drawn into the drainage lumen of the double lumen cannula and returned through an infusion lumen at the desired location. The present invention achieves minimally invasive insertion without surgical sutures to the heart, and allows for optimal drainage of the blood from the heart. With use of the double lumen cannula, it prevents need for multiple cannulation sites, and greatly reduces the blood recirculation. Removal of the cannula is simplified without need for suturing or insertion of a plugging member.

19 Claims, 12 Drawing Sheets

Related U.S. Application Data

(60) Provisional application No. 62/079,876, filed on Nov. 14, 2014.

(51) Int. Cl.
*A61M 60/857* (2021.01)
*A61M 60/861* (2021.01)
*A61M 60/148* (2021.01)

(52) U.S. Cl.
CPC .............. *A61B 2017/3419* (2013.01); *A61B 2017/3425* (2013.01); *A61M 60/148* (2021.01)

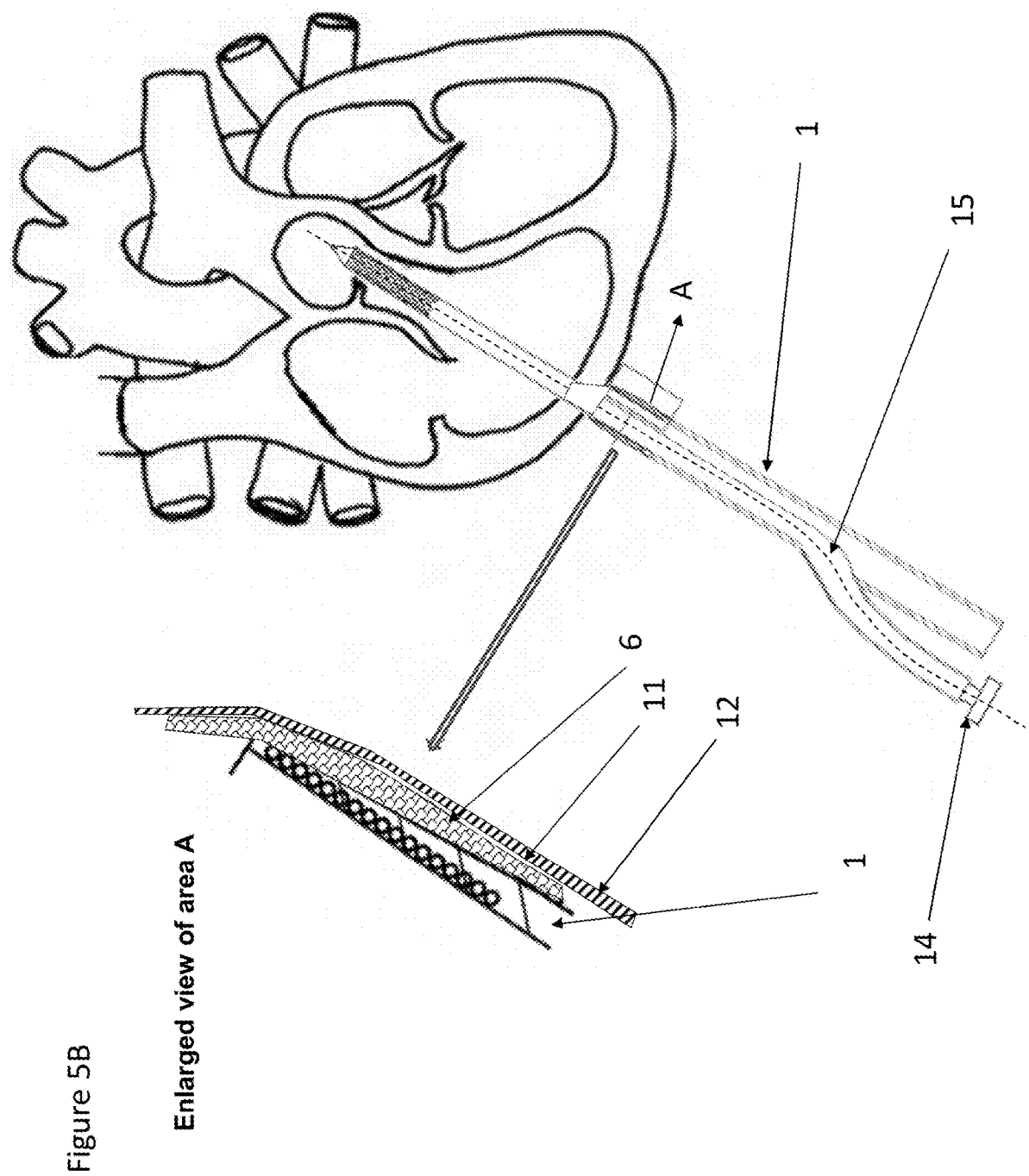

SELF-SEALING CANNULA

CROSS REFERENCE TO RELATED APPLICATION

This application is a continuation of U.S. patent application Ser. No. 15/526,107 entitled "Self-Sealing Cannula," filed with the U.S. Patent and Trademark Office on May 11, 2017, which is a national stage entry of PCT/US15/60127 entitled "Self-Sealing Cannula," filed with the U.S. Patent and Trademark Office on Nov. 11, 2015, which is based upon co-owned U.S. Provisional Patent Application Ser. No. 62/079,876 entitled "Self-Sealing Cannula," filed with the U.S. Patent and Trademark Office on Nov. 14, 2014, the specification of which is incorporated herein by reference.

GOVERNMENT LICENSE RIGHTS

This invention was made with government support under Grant Number HL082631 awarded by the National Institutes of Health. The government has certain rights in the invention.

FIELD OF THE INVENTION

The present invention relates generally to cannula systems, and more particularly to self-sealing cannula systems for blood draining and/or infusion from and to the circulatory system, and methods of use of such systems.

BACKGROUND

The human cardiovascular system serves as the material transport network in the body. It interfaces with the interstitial compartment via diffusion sites throughout the body and exchanges fluids, hormones, electrolytes, nutrients and other substances. This is achieved by the pumping function of the human heart and the blood circulation through blood vessels. The heart pumps the blood from the low-pressure venous system to the arterial side of the circulation under the proper pressure to maintain the circulatory needs of the body. The heart basically consists of four chambers: two thin-walled atria separated from each other by an interatrial septum, and two thick-walled ventricles separated by an interventricular septum. The heart is made up of two separate pump systems in series. The right atrium and ventricle act as a single unit to move venous blood from the great veins (superior vena cava (SVC) and the inferior vena cava (IVC)) to the pulmonary circulation where the venous blood becomes oxygenated by passing through the human lungs. The left atrium and ventricle act together to pump the blood from the pulmonary veins to the high-pressure systemic circulation. The blood circulates through the body and returns to the right atrium from the SVC and the IVC.

Heart failure happens when the heart cannot pump sufficient blood to meet the needs of body. Heart failure (HF) affects 5.7 million patients in the US, and it contributed to almost 280,000 deaths in 2008 (Roger et al. Circulation. 2012; 125(1): e2-220. It creates a major burden on health care providers and is expensive to treat. The estimated direct and indirect cost of HF in the United States for 2010 was $39.2 billion (2010 Heart Failure Fact Sheet from Centers for Disease Control and Prevention). Despite the advances in medical care, prognosis with HF remains poor, especially in the advanced stages. Patients with advanced HF require mechanical circulatory assistance or heart transplantation to survive. Heart transplantation is limited by the supply of donor organs. Mechanical circulatory assistance is often achieved by using ventricular assist devices (VADs), which are mechanical pumps designed to augment or replace the function of one or more chambers of the failing heart. The use of VAD, though increasing, has been limited due to the need for major operative intervention.

Further, lung disease is the #3 killer in the United States, responsible for 1 in 6 deaths (American Lung Association). Annually 400,000 deaths are attributed to pulmonary causes in spite of $154 billion in expenditure (Sanovas. "Lung Disease".). Lung failure occurs acutely or chronically. Chronic obstructive pulmonary disease (COPD) is one of the most common lung diseases and the 4th leading cause of death in the U.S. Adult Respiratory Distress Syndrome (ARDS) is commonly afflicting 190,000 patients yearly and the average survival rate is between 30-50% (Rubenfeld et al. N Engl J Med 2005; 353:1685-93). If lung failure occurs, either mechanical ventilation or extracorporeal membrane oxygenation (ECMO) must be implemented to oxygenate the blood to maintain the need of the body for oxygen. Mechanical ventilation is effective for short-term support, yet the sustained tidal volumes and airway pressures often used may damage the lungs. The ECMO closely simulates physiological gas exchange, but requires cannulation to access the blood.

In current clinical practices, the use of VAD and ECMO both require major invasive surgical procedures to implant these devices via a set of cannulae. Thus, only a limited population of patients receives these device-based therapies. A cannula is a medical tube inserted into the body for drainage and infusion of blood. The major problems of the available cannulae for ECMO are (U.S. Pat. No. 7,473,239 B2 to Wang et al): 1) multiple cannulation needs and insertion of cannulae with larger diameters cause extra trauma to patients; 2) when blood is drawn and reinfused from the right atrium or central veins, blood recirculation leads to insufficient extracorporeal oxygenation; 3) the placement of the drainage lumen against the vein causes insufficient venous blood drainage; and 4) direct cannulation of the heart can result in hemorrhage from fixating surgical sutures. Similarly, the currently available cannulae for VADs also have a similar problem of extra trauma. Therefore, a minimally invasive, efficient and simple percutaneous cannula system is needed for ECMO and VAD.

SUMMARY OF THE INVENTION

The present invention discloses a self-sealing cannula which can be configured as either a double lumen cannula or a single lumen cannula. FIG. 1 shows the self-sealing cannula as a double lumen cannula (DLC). The self-sealing DLC has a drainage cannula and infusion cannula, a self-sealing double umbrella made of wire mesh, and a self-closing iris made of wire mesh. The self-sealing DLC can be used to draw blood directly from the right ventricle through a drainage lumen by a minimally invasive surgery through the pericardium and infuses the blood to the pulmonary artery via an infusion lumen. This configuration can be used for ECMO respiratory support or mechanical circulatory support of the right heart. The infusion lumen has a smaller diameter than the drainage lumen and is placed partially inside of the drainage lumen. A competent (non-regurgitant) native semilunar valve between the ventricle and artery serves to minimize flow "recirculation"—or regurgitation of arterial outflow retrograde into the ventricular inflow. The cannula can also be used to draw blood from the left ventricle and return blood to the aorta for mechanical circulatory support of the left heart. Inside of the closure formed by the wire meshes of the double umbrella and the iris, hemostatic felt is incorporated for hemostasis.

A double-umbrella (disc) structure is placed around the drainage cannula tip to provide hemostasis after the DLC is inserted into the right heart (FIG. 1). The double disc structure is made from a wire mesh and can be squeezed into a sheath introducer along with the dual lumen cannula. When the mesh is released from the sheath introducer, it can expand slightly in the radial direction and shrink in the axial direction to seal the insertion site on the ventricular wall and to conform the epicardial and endocardial walls, instead of the conventional surgical sutures which need a larger insertion site and require an open chest procedure. Therefore, the cannula can be simply placed into the heart through a small hole across the pericardium, reducing the complication of surgery and trauma to the patients. The infusion and drainage lumen of the DLC can be placed though a conventional needle punch and a guide catheter which can be a Swan-Ganz type. After the needle punch, the guide catheter is advanced into the pulmonary artery. Through the guide catheter, the infusion lumen tip is advanced into the pulmonary artery using a dilator. As the infusion lumen tip is advanced, a sheath containing the DLC can act as an introducer/dilator to further expand the insertion site. Once the drain tip is appropriately positioned, the sheath is removed. The double-umbrella recoils back to its pre-set double umbrella shape to seal the insertion site and to secure the DLC on the ventricular wall.

Once the dual lumen cannula is placed on the heart, fixed on the diaphragm or muscle layer at the incision site and exited the skin, a VAD can be connected to provide the heart support, or an ECMO system can be attached to provide respiratory support. The same procedure can be performed on the left heart for left heart support. The self-sealing cannula can likewise be configured as a single lumen cannula for blood drainage or infusion.

Deployment of the cannula may be performed via minimally invasive surgical and endovascular techniques:

(a) Small-incision ventricular access: a subxiphoid approach is used to access the diaphragmatic surface of the right ventricle, whereas a left mini-thoracotomy or subcostal incision is used to access the left ventricular apex. The cannula is designed to be placed without utilization of temporary cardiopulmonary bypass; this is advantageous particularly for left-sided support, since current paracorporeal ventricular assist devices with left ventricular cannulation generally require institution of cardiopulmonary bypass for placement.

(b) Seldinger-based ventricular and arterial access: the ventricle is accessed using a hollow-bore needle, through which a guidewire/guide catheter is passed into the ventricular cavity and thence into the distal outflow artery under fluoroscopic and/or transesophageal echocardiographic guidance. Graduated serial dilations are performed until the self-sealing double umbrella loaded in a sheath and over the guidewire/guide catheter is placed and locked into position to seal the insertion access after being released, in a way similar to the manner in which a ventricular septal occluder seals a defect circumferentially with a diameter wider than that of the ventriculotomy both inside and outside the ventricular cavity.

(c) Cannula loading and positioning: the cannula is preloaded and packaged with a sheath, dilators and a guidewire/catheter. Under fluoroscopic/echocardiographic guidance based upon markers present on the cannula, the cannula is positioned such that the distal portion of the infusion cannula is present within the proximal portion of the artery, whereas the distal portion of the drainage cannula is present within the ventricular cavity. A locking mechanism secures the cannula at the desired position to the double umbrella disk. In the case of a single lumen cannula, the distal tip of the cannula is present in the ventricular cavity.

(d) Cannula removal: the cannula can be removed through a thread locking mechanism between the outer surface of the cannula body and the central hole of the double umbrella. An inner iris recoils to fill the central hole to act as a valve once the cannula body is removed.

BRIEF DESCRIPTION OF THE DRAWINGS

The numerous advantages of the present invention may be better understood by those skilled in the art by reference to the accompanying figures in which:

FIG. 5B is a schematic view of the DLC of FIG. 1 during dilation of the insertion site with the second dilator for placement of the drainage cannula of the self-sealing DLC into the right ventricle.

DETAILED DESCRIPTION OF THE PREFERRED EMBODIMENTS

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
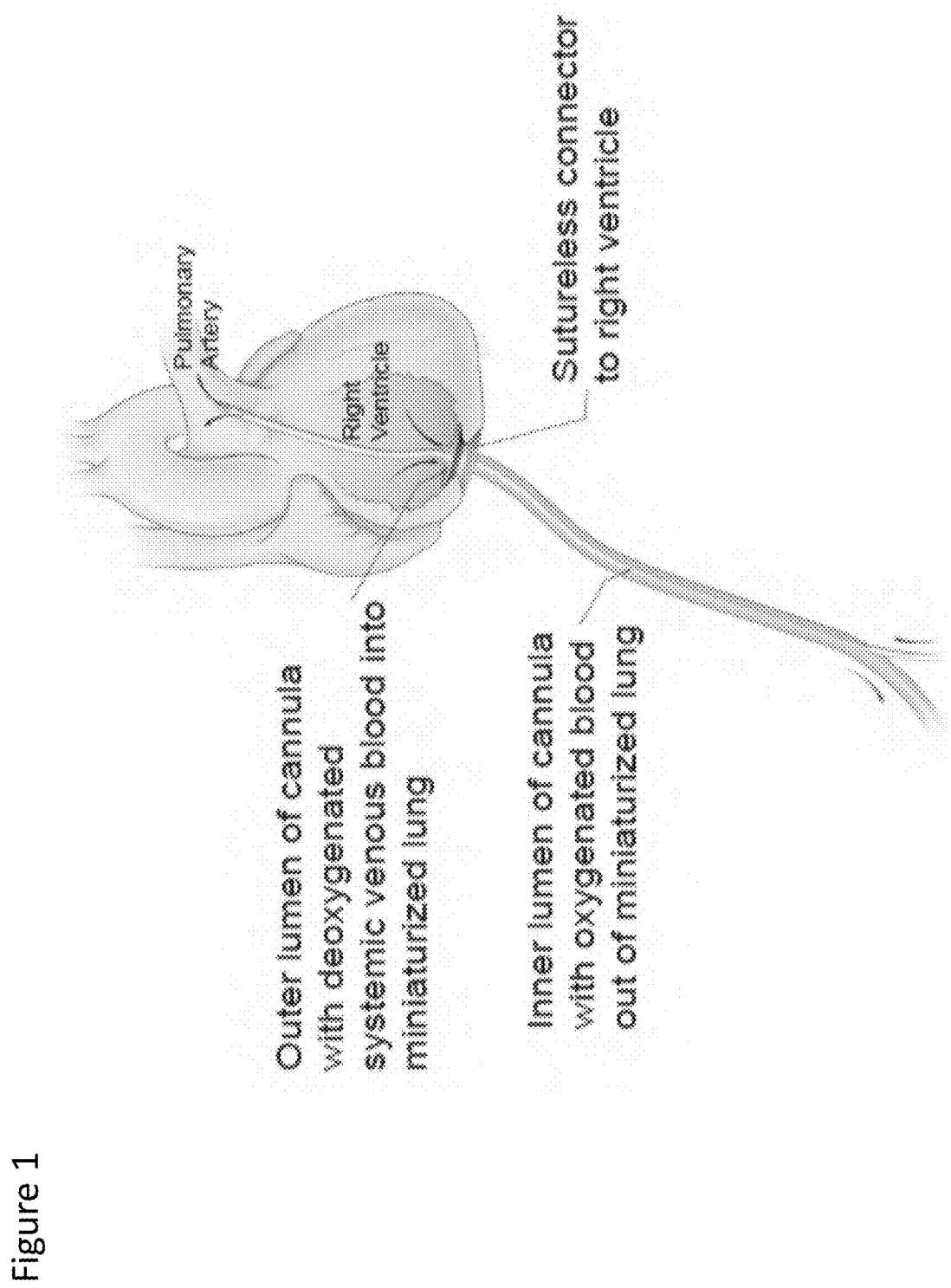
FIG. 1 is a schematic view of a double lumen cannula ("DLC") assembly placed into the right heart and pulmonary artery and including a self-sealing cannula in accordance with aspects of an embodiment of the invention.

FIG. 1 is a schematic view of a self-sealing cannula in accordance with aspects of an embodiment of the invention, and more particularly a self-sealing double lumen cannula (DLC) configured to draw blood from the right ventricle through the outer lumen of the DLC and to return the blood to the pulmonary artery. A double umbrella fixture serves as the sutureless self-sealing mechanism and the holder of the DLC in place on the right ventricle.

Figure 2A:
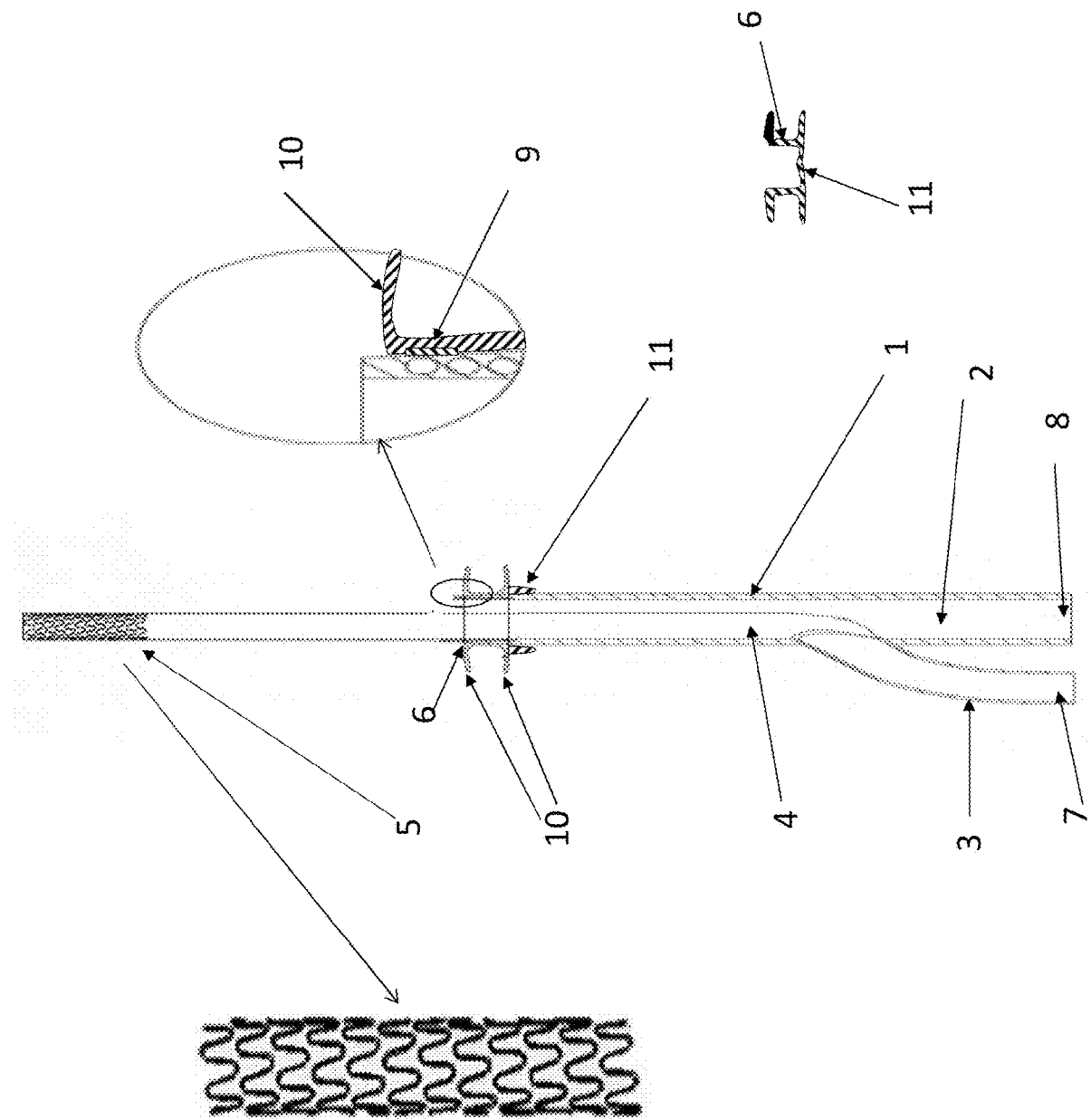
FIG. 2A is a close-up, cross-sectional view of the self-sealing DLC of FIG. 1 and its components.

In accordance with certain aspects of an embodiment of the invention, a DLC assembly is shown in FIG. 2. The DLC assembly 1 includes a circular drainage cannula whose internal surface forms a drainage lumen 2, a side fused tubular cannula 3 whose internal surface forms the infusion lumen 4, and a compressible double umbrella 6. The infusion cannula comprises a regular thick wall infusion port 7, a thin wall circular tube 4 embedded on the sidewall of the drainage lumen, and an extended circular portion 5. A portion of the infusion cannula runs through the lumen of the drainage cannula. The extended portion 5 is a thin wall circular tube, but re-enforced with a wire frame so that it is strong in the radial direction, but flexible and conforming in the axial direction. Furthermore, a small section of the extended infusion cannula 5 comprises a naked zig-zig wireframe (as shown) so that the returned blood from the infusion lumen can be distributed axially and radially in the targeted blood vessel and the returned blood flow is not blocked when the distal tip is positioned against the vessel wall. The double umbrella 6 is attached to the drainage cannula body. The double disc-like umbrella 6 comprises a pair of outer unfolding wire mesh umbrellas 10, a metal ring 9 and an inner recoiling wire mesh iris 11 (similar in configuration to a camera iris or shutter). The wire meshes are preferably formed of a shape memory alloy that may be compressed radially to a diameter less than its intended diameter during deployment, and recover to its intended functional shape when warmed to its transformation temperature as a result of the patient's own body temperature. In an embodiment of the invention, the wire mesh of the double umbrella 6 is particularly formed from Nitinol, an alloy typically made of approximately 55%-56% nickel and 44%-45% titanium by weight. The exterior configuration of double umbrella 6 is somewhat similar to atrial and ventricular septal defect occluder devices, such as the Amplatzer occluder device available from AGA Medical Corp. of Golden Valley, Minnesota, but as described in greater detail herein is significantly improved to provide for its use with a cannula assembly and allowing self-sealing after removal of a cannula that extends through the double umbrella 6.

Nitinol is an alloy of nickel and titanium. Nitinol has a superelastic property, which refers to the ability of recovering to its original shape above a certain temperature (transformation temperature) after a deformation at a lower temperature. A process called shape setting is used to make Nitinol remember a desired shape. Usually, this process comprises tightly constraining the material into the desired shape on a mandrel at 450-550° C. for 10-80 minutes depending on the Nitinol material from different brands, which process is known to persons skilled in the art. In at least one embodiment, the best condition of heat treatment for the Nitinol wire (Johnson Matthey Inc., West Chester, PA) with a diameter of 0.01 inch in cross-section is 500° C. for 70 minutes, which can make its transformation temperature equal to 27° C. In other embodiments, the transformation temperature can be between 30° C. and 37° C. Below the transformation temperature, the material is not stable and its shape can be changed easily. Cannula assemblies incorporating Nitinol wire mesh configurations, and methods of their use and manufacture, are described in international PCT Application No. PCT/US14/46978 titled "Self-Expanding Cannula," the specification of which is incorporated herein by reference in its entirety.

Figure 2B:
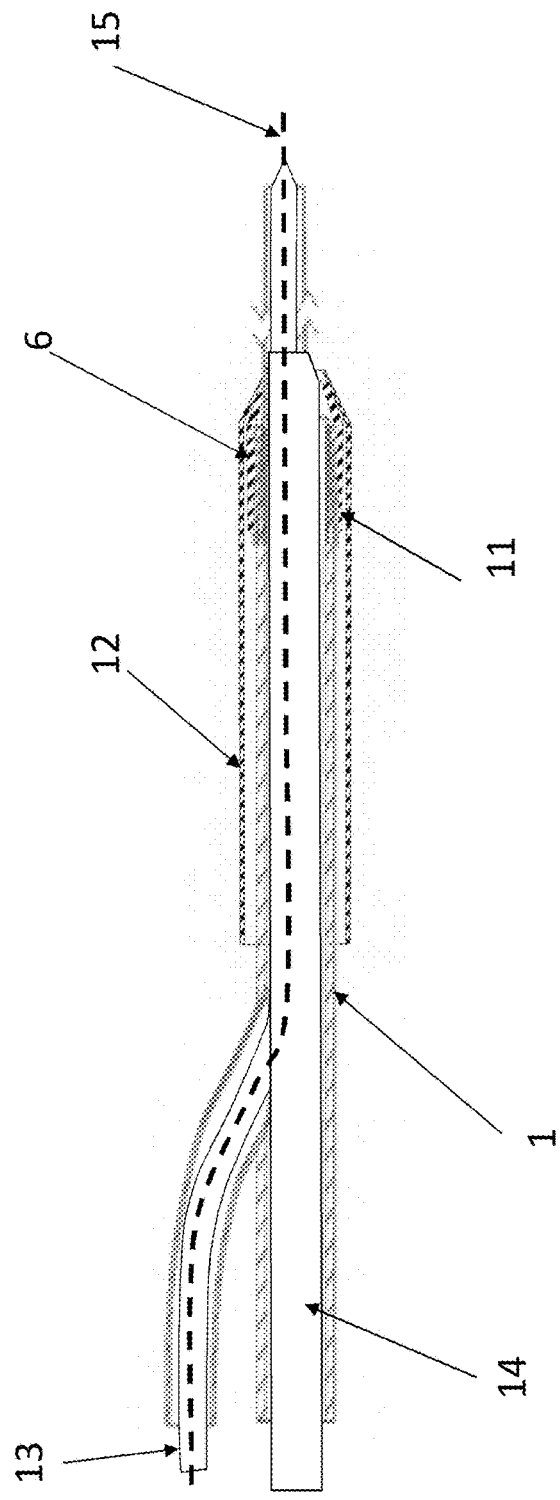
FIG. 2B is a close-up, cross-sectional view of the self-sealing DLC of FIG. 1 packaged in a sheath with two dilators and a guide catheter.

Alternatively, the wire mesh may be sufficiently flexible so as to allow it to be radially compressed (such as by inserting the wire mesh and cannula into a tearable sheath for initial insertion of the cannula into a patient's ventricle, as further described below) and thereafter return to its expanded, normal shape after such radial compression is removed. When the wire mesh is released from the sheath introducer, it can expand in the radial direction to seal the insertion site on the ventricular wall and to conform to the epicardial and endocardial walls. Similarly, the iris 11 is preferably formed of the same shape memory alloy wire mesh as the double umbrella. A metal circular ring 9 may be attached to the wire mesh to provide a lock mechanism for the drainage cannula body to be affixed to the double umbrella 6. A male thread is preferably formed on the outer circular surface of the drainage cannula. A matching female thread is preferably formed on the inner surface of the ring of the double umbrella. Thus, the DLC can be locked in place or removed from double umbrella 6 by threading in or out. The iris 11 of the double umbrella 6 functions as the self-sealing shutter, which is similar to the circular shutter of a camera. When the DLC is in use, the iris is forced to expand by the drainage cannula body. When the drainage cannula is removed, the iris recoils back to close the central hole of the double umbrella 6. The drainage cannula tip is preferably made of biocompatible metal, such as titanium, and flush-mounted on the double umbrella 6. Therefore, the drainage tip slightly extrudes from the ventricular wall to provide excellent blood drainage and prevent tissue overgrowth into the cannula lumen. The remaining portion of the cannula is made of biocompatible polymer, such as polyurethane, PVC, etc. The circular body of the drainage cannula is wire re-enforced. The metal tip and cannula body are molded and fused together. FIG. 2B shows the self-sealing DLC 1 assembled in a sheath 12 with two dilators 13 and 14 and a guide catheter 15. The double umbrella 6 and its iris 11 are compressed in the sheath 12.

Alternatively, a section of vascular graft with the pre-set purse-string suture may be sewn on the double umbrella to serve the function of the above mentioned iris to seal the central hole of the double umbrella after the cannula body is removed. When the drainage cannula body is withdrawn from the double umbrella by unlocking the thread, the double purse-string is pulled and ligated the graft lumen to seal the hole.

Figure 3B:
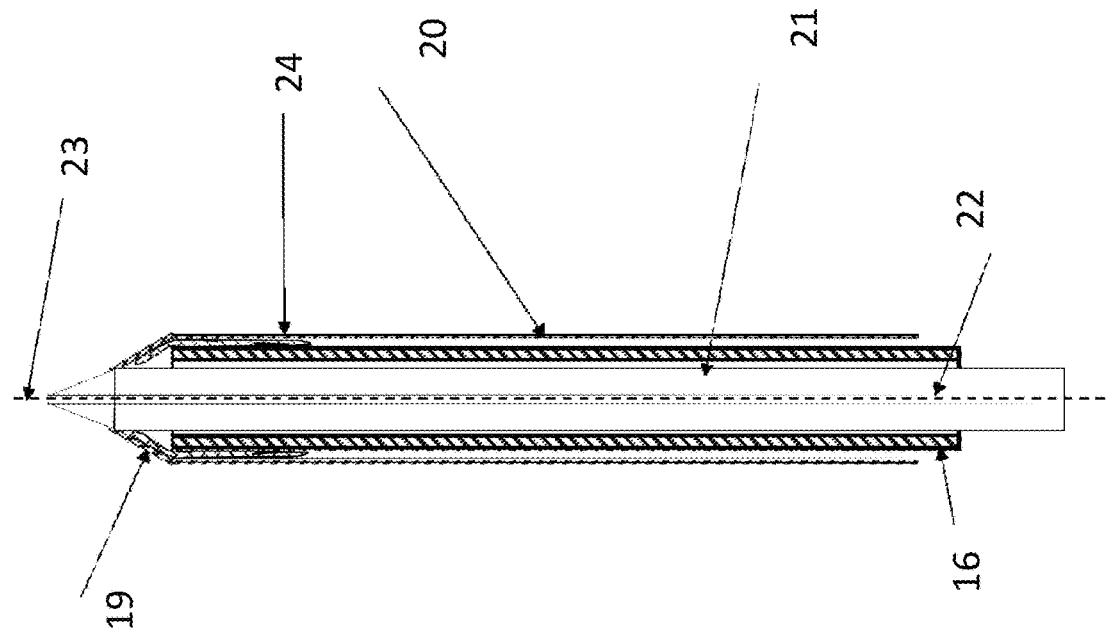
FIG. 3B is a close-up, cross-sectional view of the self-sealing single lumen cannula of FIG. 3A packaged in a sheath with a dilator and a guidewire.
Figure 3A:
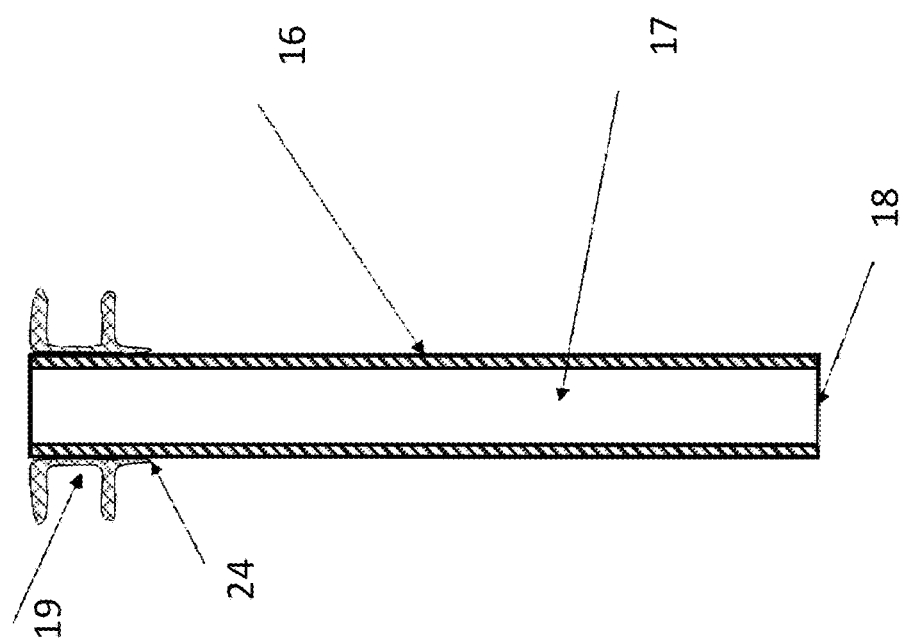
FIG. 3A is a close-up, cross-sectional view of a self-sealing single lumen cannula in accordance with further aspects of an embodiment of the invention.

In accordance with certain aspects of an embodiment of the invention, a single lumen cannula assembly is shown in FIG. 3A. The self-sealing single lumen cannula comprises a circular tube 16 whose internal surface 17 forms the drainage lumen or infusion lumen and a double umbrella 19 with iris 24. The proximal end is the connector port 18. FIG. 3B shows the self-sealing single lumen cannula 16 assembled in a sheath 20 with a dilator 21 whose central hole 22 is configured for passing a guide catheter or a guidewire 23. The double umbrella 19 is compressed by the sheath 20 and the iris 24 is expanded by the cannula body in the sheath 20. In this configuration, the single lumen cannula preferably includes a threaded connection to the interior of double umbrella 19 of similar configuration to that described above with respect to the DLC.

Figure 4A:
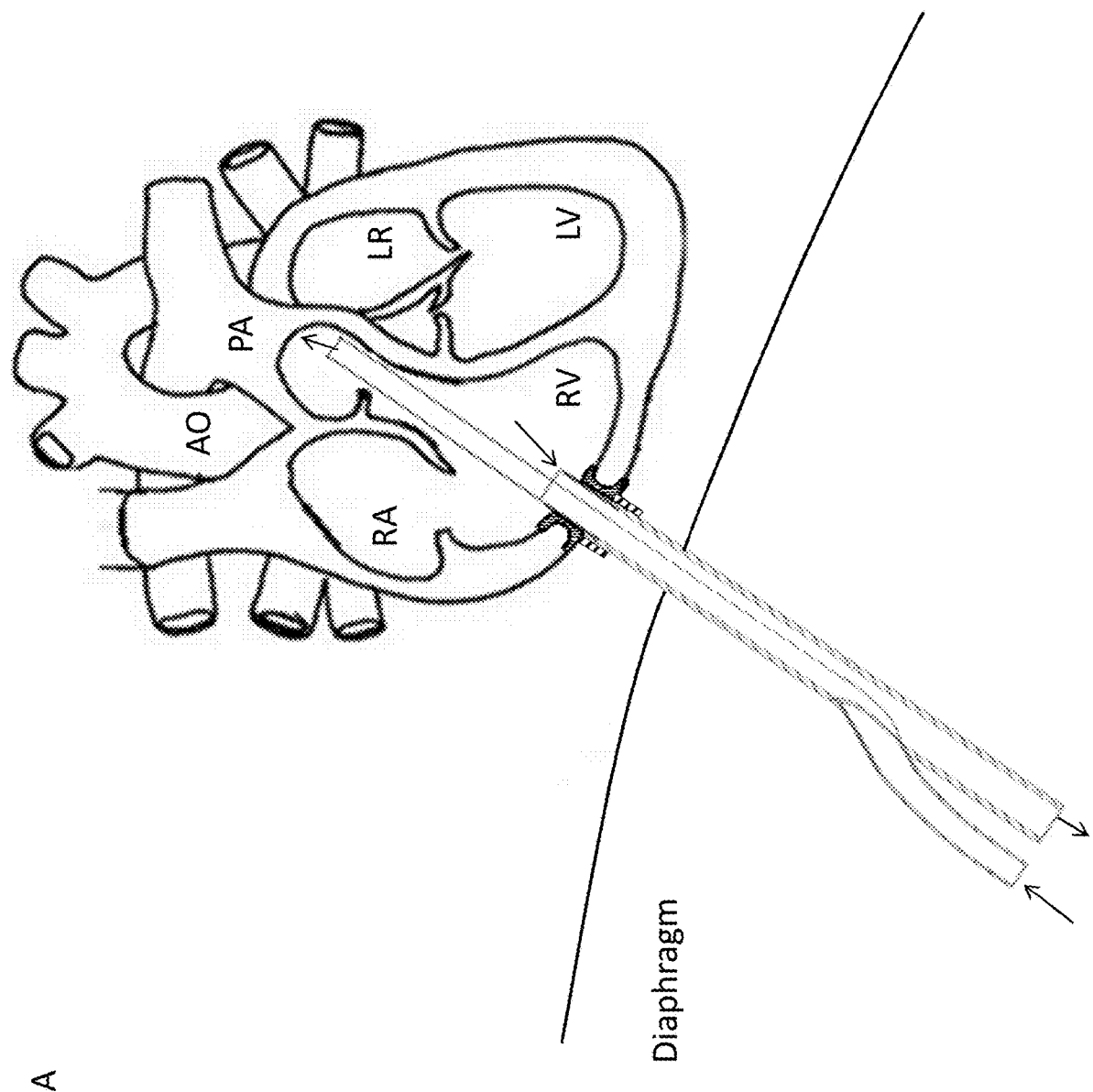
FIG. 4A is a schematic view of the self-sealing DLC of FIG. 1 placed into the right ventricle and pulmonary artery.

FIG. 4A is a schematic, cross-sectional view of the DLC placed on the right ventricular wall to draw blood from the right ventricle through the drainage lumen of the DLC and to return the blood to the pulmonary artery through the infusion lumen of the DLC. The double umbrella fixture seals the insertion site on both the endocardium side and the epicardium side through the pre-formed flexible and conforming double umbrella wire mesh. The self-seal iris is expanded.

Figure 4B:
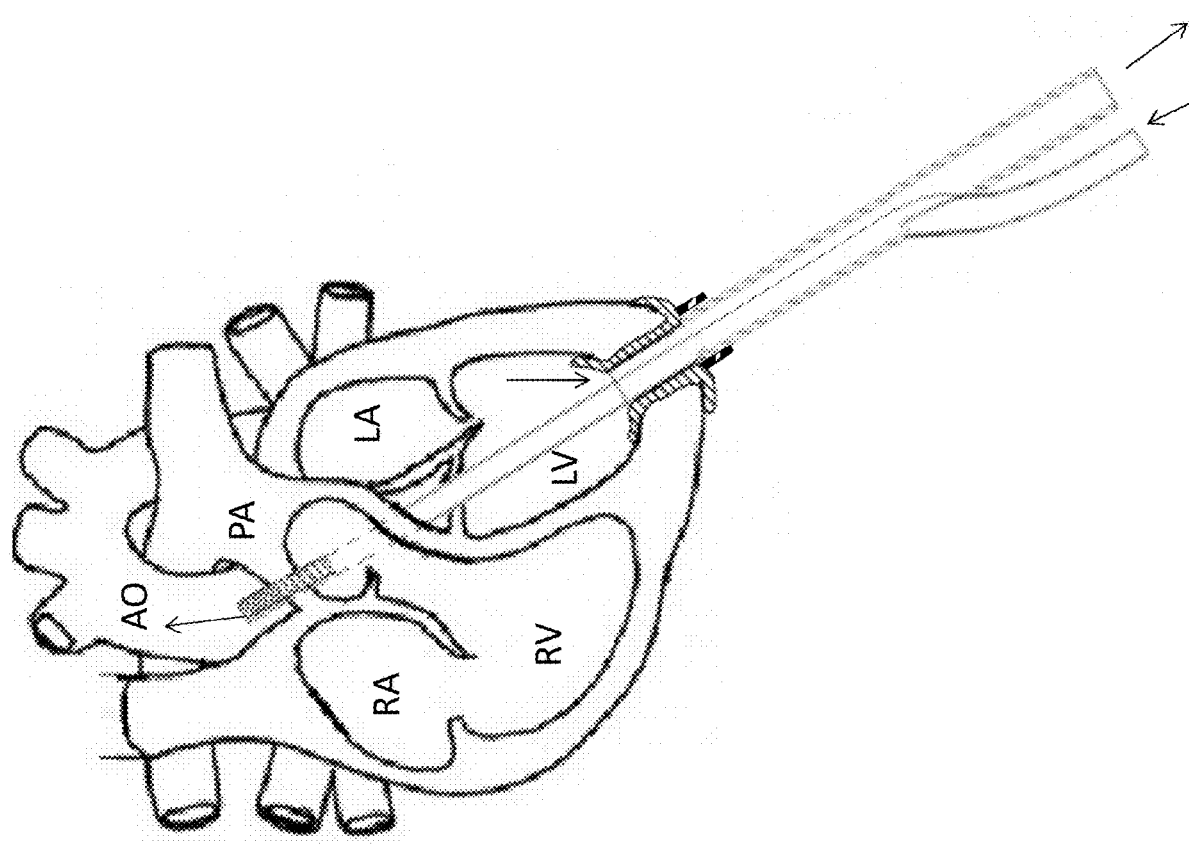
FIG. 4B is a schematic view of the self-sealing DLC of FIG. 1 placed into the left ventricle and aorta.

FIG. 4B is a schematic, cross-sectional view of a DLC placed on the left ventricular apex to draw blood from the left ventricle through the drainage lumen of the DLC and return the blood to the aorta through the infusion lumen of the DLC. The flexible and conforming double umbrella again is placed on the apex and seals the insertion site. The DLC is placed in the same fashion as placed in the right ventricle as described above.

Figure 4C:
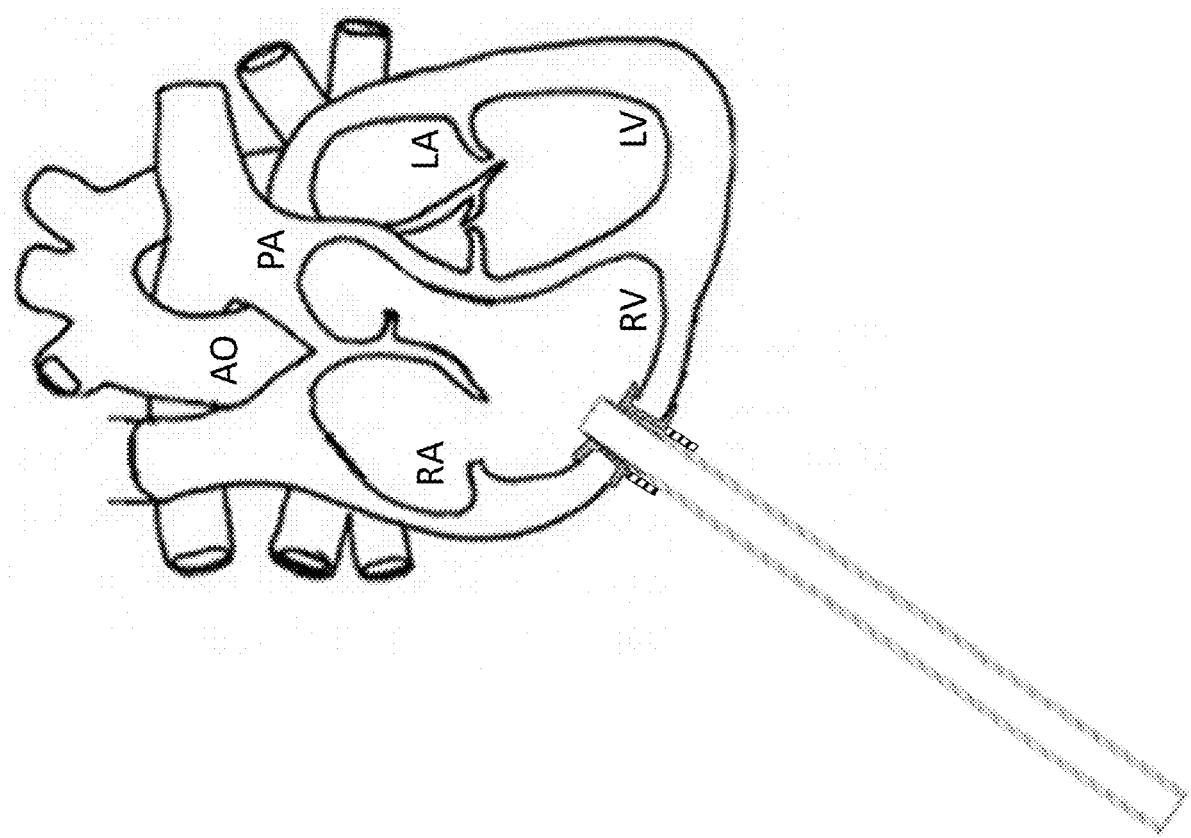
FIG. 4C is a schematic view of the self-sealing single lumen cannula of FIG. 3A placed into the right ventricle as a drainage cannula.

FIG. 4C is a schematic, cross-sectional view of the self-sealing cannula configured as a single lumen cannula which is placed on the right ventricle wall to draw blood from the right ventricle. The same self-sealing conforming double umbrella seals the insertion site.

Figure 5A:
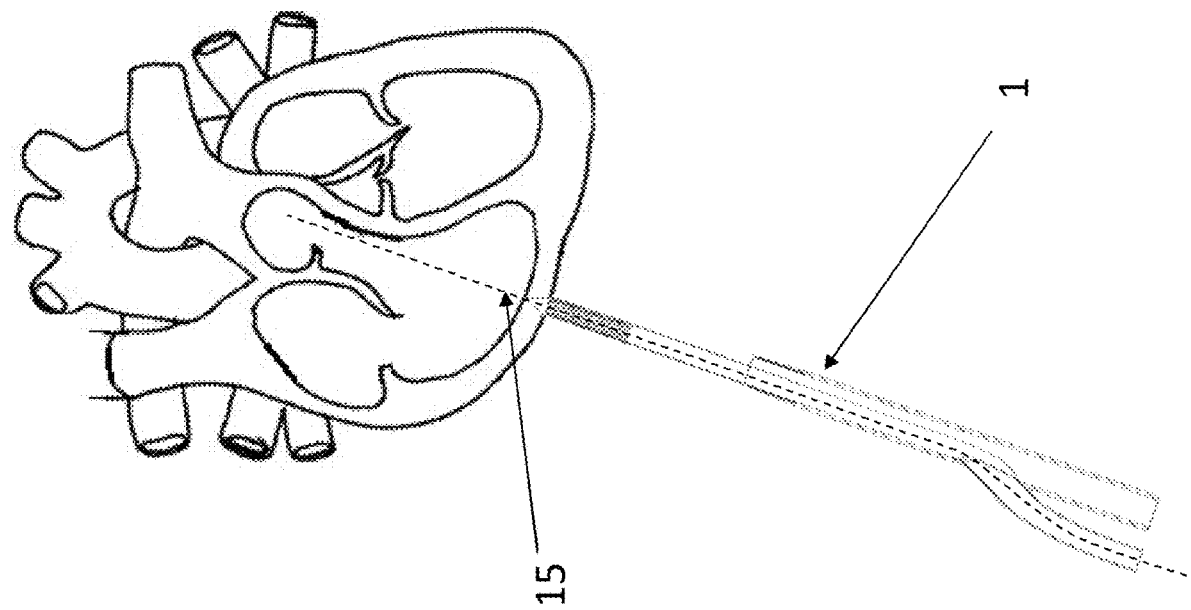
FIG. 5A is a schematic view of the DLC of FIG. 1 during dilation of the insertion site with the first dilator for placement of the infusion cannula of the self-sealing DLC into the right ventricle.
Figure 5C:
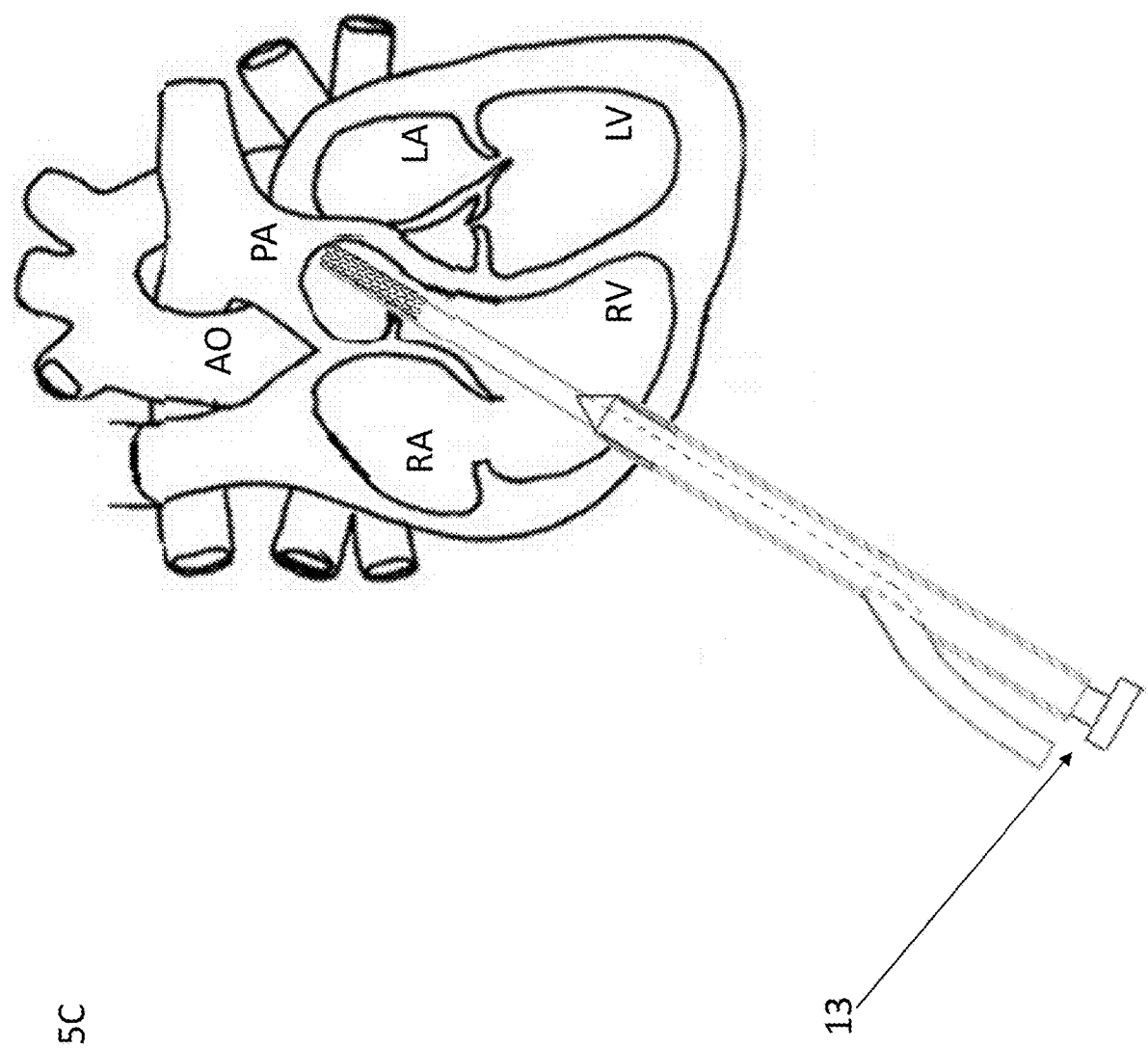
FIG. 5C is a schematic view of the DLC of FIG. 1 during its placement into the right ventricle and pulmonary artery.
Figure 5D:
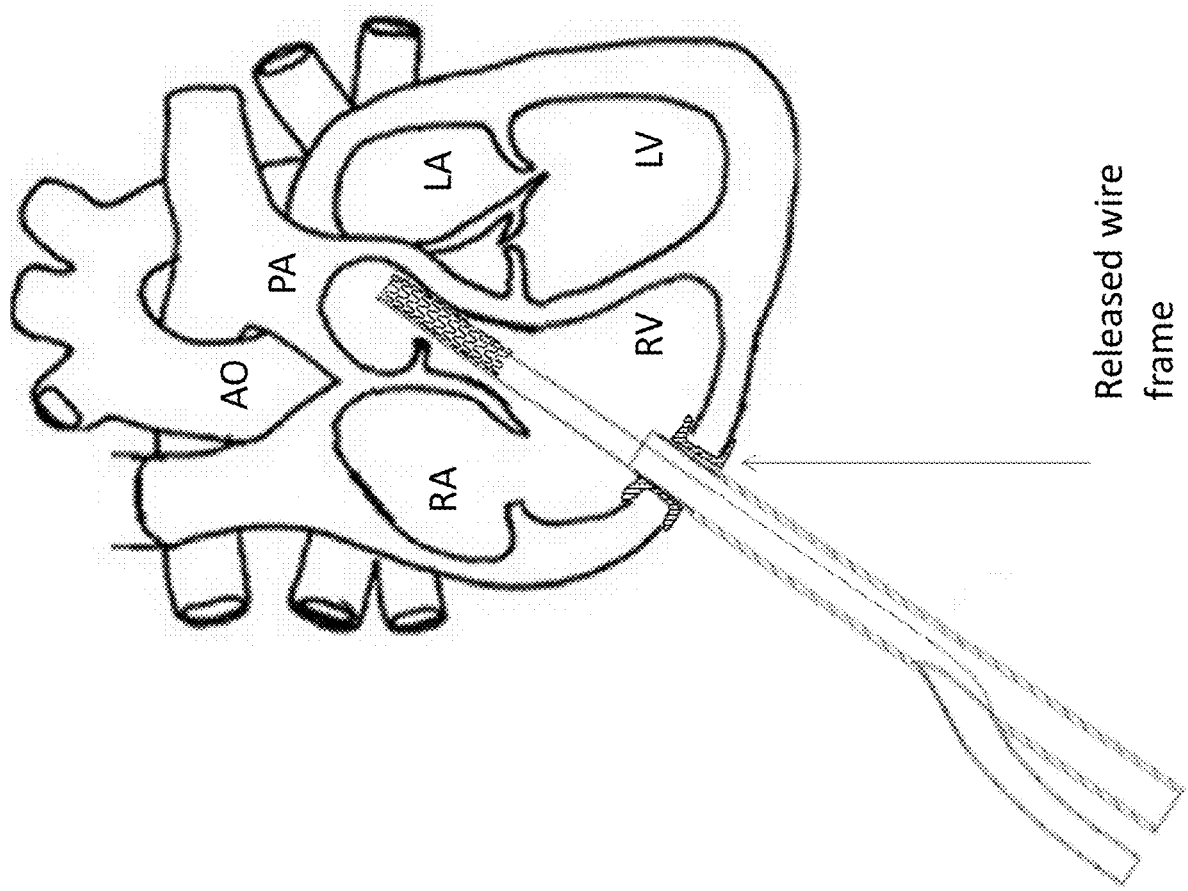
FIG. 5D is a schematic view of the DLC of FIG. 1 following its placement into the right ventricle and pulmonary artery.
Figure 5E:
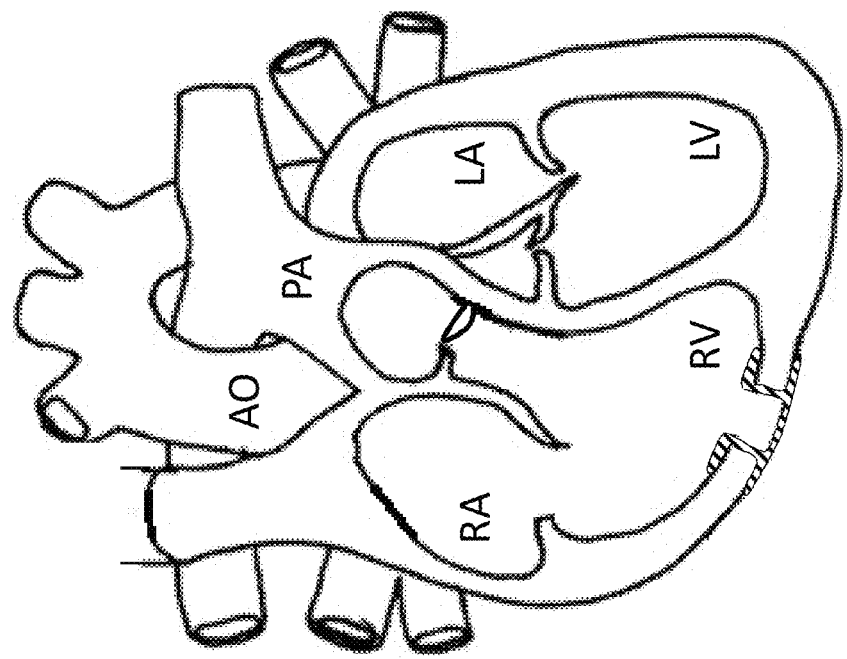
FIG. 5E is a schematic view of the self-seal mechanism of FIG. 1 using the double umbrella after the DLC is removed from the right ventricle.

FIG. 5A-E show the deployment and removal of a self-sealing DLC according to aspects of an embodiment of the invention into the right ventricle and pulmonary artery. A needle is used to punch the right ventricle for passing a guidewire. A Swan-Ganz type balloon catheter can be used to run through a central lumen of the dilator inside the infusion lumen. The balloon guide catheter with an inflatable balloon is then inserted into the right ventricle and advanced into the pulmonary artery with the aid of the inflated balloon and the guidewire. Once the guidance catheter is in place (which can be verified by fluoroscope or echocardiography), the infusion lumen cannula with its dilator is advanced into contact with the right ventricular epicardium by following the guide catheter (FIG. 5A). Through its progressive conical tip of the dilator, the needle punch site is gradually enlarged as the infusion cannula is pressed into the right ventricle and then advanced into the pulmonary artery. At this time, the second dilator for the drainage lumen is approaching the insertion site (FIG. 5B). Through the semi-conical shape of the dilator, the insertion site is further enlarged by the dilator to allow the tip of the sheath of the DLC to advance into the right ventricle (FIG. 5C). Once the first half of the compressed double umbrella is located in the right ventricle, the sheath of the DLC can be withdrawn. A tearable sheath can be used here. After the sheath is removed, the first umbrella of the double umbrella unfolds inside the right ventricle and conforms to the endocardium. The second umbrella likewise unfolds outside the right ventricle and conforms to the epicardium once the sheath is completely removed (FIG. 5D). Then the DLC is in place for connection to a VAD for mechanical circulatory support or an ECMO system for respiratory support. If the support is no longer needed, the DLC can be removed by un-threading the cannula body and withdrawing the cannula body. Once the cannula body is out of the right ventricle, the iris on the exterior portion of the double umbrella (which has been expanded by the cannula body) recoils to its pre-formed shape to seal the central opening of the double umbrella (FIG. 5E).

Similarly, a DLC having the above features can be placed into the left ventricle (FIG. 4B) using the same approach. For the single lumen cannula, only one dilator is needed. The approach described above can be easily adapted for placing the single lumen cannula (FIG. 4C). Once the DLC or the single lumen cannula is placed in the circulation system, the respective ports (drainage port and infusion port) are connected to a VAD for heart support or an ECMO system for respiratory support.

Advantages of the invention may include any of the following:
1. Minimally invasive insertion and sutureless self-sealing of direct heart cannulation;
2. Avoidance of multiple heart cannulation sites;
3. Drainage unimpeded by vein and wall obstruction;
4. Less possibility of thrombosis and flush mounted drainage tip; and
5. Minimal blood recirculation.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:
1. A self-sealing cannula system, comprising:
an elongated first cannula; and
a flexible, self-sealing closure attached to said first cannula, said closure comprising a hollow, elongate structure defining an open interior and a first connector on an interior of said open interior, said first cannula having a second connector configured for removable attachment to said first connector, and wherein said closure further comprises an integrally-formed self-sealing shutter;
wherein said self-sealing closure is configured to expand radially from a compressed state to an uncompressed state, wherein in said uncompressed state said self-sealing closure is configured to seal against an interior surface and an exterior surface of an insertion site of said first cannula; and
wherein said self-sealing shutter is further configured to close a central hole of the shutter when the first cannula is not inserted therein, and is expandable to open when the first cannula is inserted therein.
2. The self-sealing cannula system of claim 1, wherein said first connecting member and said second connecting member comprise a mating threaded connection.
3. The self-sealing cannula system of claim 1, further comprising a removable sheath encasing said self-sealing closure and at least a portion of said first cannula.
4. The self-sealing cannula system of claim 3, wherein said removable sheath compresses said self-sealing closure into said compressed state, and wherein said self-sealing closure is further configured to automatically expand from said compressed state to said uncompressed state upon removal of said sheath within a patient's body.
5. The self-sealing cannula system of claim 4, wherein said self-sealing closure is temperature-responsive and further configured to expand from said compressed state to said uncompressed state in response to a patient's body temperature.
6. The self-sealing cannula system of claim 1, wherein said self-sealing closure further comprises a self-closing iris at an end of said self-sealing closure.

7. The self-sealing cannula system of claim 6, wherein said iris is configured to automatically close said end of said self-sealing closure upon removal of said first cannula from said self-sealing closure.

8. The self-sealing cannula system of claim 1, further comprising:
a second cannula positioned within said first cannula and extendable from said first cannula.

9. The self-sealing cannula system of claim 8, said second cannula having an end formed of an expandable wire frame.

10. The self-sealing cannula system of claim 9, wherein said expandable wire frame of said second cannula is temperature responsive and configured to expand in response to a patient's body temperature.

11. The self-sealing cannula system of claim 8, further comprising a blood pump attached to said first cannula, and a blood oxygenator attached to said second cannula.

12. The self-sealing cannula system of claim 1, wherein said self-sealing closure is formed of temperature responsive wire mesh.

13. The self-sealing cannula system of claim 12, wherein said wire mesh further comprises a superelastic Nitinol alloy.

14. The self-sealing cannula system of claim 1, wherein said self-sealing shutter is affixed to a bottom end of a wall of said hollow, elongate structure of said self-sealing closure.

15. A self-sealing cannula system, comprising:
an elongated first cannula; and
a flexible, self-sealing closure attached to said first cannula, said closure comprising a hollow, elongate structure defining an open interior, wherein said first cannula is removably attached to said interior of said closure, and wherein said closure further comprises an integrally-formed self-sealing shutter;
wherein said self-sealing closure is configured to expand radially from a compressed state to an uncompressed state, wherein in said uncompressed state said self-sealing closure is configured to seal against an interior surface and an exterior surface of an insertion site of said first cannula; and
a second cannula positioned within said first cannula and extendable from said first cannula.

16. The self-sealing cannula system of claim 15, said second cannula having an end formed of an expandable wire frame.

17. The self-sealing cannula system of claim 16, wherein said expandable wire frame of said second cannula is temperature responsive and configured to expand in response to a patient's body temperature.

18. The self-sealing cannula system of claim 15, further comprising a blood pump attached to said first cannula, and a blood oxygenator attached to said second cannula.

19. The self-sealing cannula system of claim 15, wherein said self-sealing closure further comprises a self-closing iris at an end of said self-sealing closure, wherein said iris is configured to automatically close said end of said self-sealing closure upon removal of said first cannula from said self-sealing closure.

* * * * *